United States Patent [19]

Lipton

[11] Patent Number: 5,053,419

[45] Date of Patent: Oct. 1, 1991

[54] TREATMENT OF AIDS DEMENTIA, MYELOPATHY AND BLINDNESS

[75] Inventor: Stuart A. Lipton, Newton, Mass.

[73] Assignee: The Children's Medical Center Corporation, Boston, Mass.

[21] Appl. No.: 502,296

[22] Filed: Mar. 30, 1990

Related U.S. Application Data

[63] Continuation-in-part of Ser. No. 331,872, Mar. 31, 1989, abandoned.

[51] Int. Cl.$^5$ .............................................. A61K 31/44
[52] U.S. Cl. .................................................... 514/356
[58] Field of Search .......................................... 514/356

[56] References Cited

PUBLICATIONS

Brenneman et al., 1988, Nature, 335:639.
Price et al., 1988, Science, 239:586.
Ho et al., 1989, Annals in Internal Medicine, 111:400.
Pomerantz et al., 1987, New Eng. J. Med., 317:1643.

*Primary Examiner*—Stanley J. Friedman

[57] ABSTRACT

A method of reducing death of CNS neurons in a human patient infected with a human immunodeficiency virus, involving administering to the patient a compound capable of reducing the gp120-responsive rise in free $Ca^{++}$ ion concentration in the CNS neurons of the patient, in a concentration effective to cause such reduction.

10 Claims, 6 Drawing Sheets

TREATMENT OF AIDS DEMENTIA, MYELOPATHY AND BLINDNESS

BACKGROUND OF THE INVENTION

This application is a continuation in part of U.S.S.N. 331,872, filed Mar. 31, 1989, now abandoned.

This invention relates to the treatment of central nervous system disorders caused by infection with human immunodeficiency virus type I (HIV-I).

HIV-I infection in humans causes general immunosuppression and involves other disorders, such as blindness, myelopathy, or a dementing neurological disorder, i.e., the AIDS dementia complex, the latter of which is a common and important cause of morbidity in patients in advanced stages of infection. HIV-I infection has been documented in various areas of the CNS, including the cerebral crotex, spinal cord, and retina. Price et al. (1988, Science 239:586) and Ho et al. (1989, Annals in Internal Medicine 111:400) review the clinical, epidemiological, and pathological aspects of the AIDS dementia complex, and suggest that the mechanism underlying the neurological dysfunction may be indirect tissue damage by either viral- or cellular-derived toxic substances released by infected cells.

Pomerantz et al. (1987, New Eng. J. Med. 271:1643) document the presence of HIV type I infection of the retina in two patients with AIDS. Brenneman et al. (1988, Nature 335:639) found gp120, the coat protein of HIV, killed hippocampal neurons.

SUMMARY OF THE INVENTION

The invention features a method of reducing death of CNS neurons in a human patient infected with a human immunodeficiency virus, by administering to the patient a compound capable of reducing the gp120 responsive rise in intracellular free $Ca^{++}$ion concentration in CNS neurons of the patient, in a concentration effective to cause such reduction.

Preferably, the blood of the infected patient contains antibodies to HIV 1; most preferably, the patient manifests symptoms of AIDS related complex or of acquired immune deficiency syndrome. The method may also include administration of a second compound that is capable of reducing the gp120 responsive rise in intracellular free $Ca^{++}$ion concentration. The compounds most preferred are calcium channel antagonists capable of crossing the blood brain barrier; these may be administered orally or intravenously; of these compounds, nimodipine is currently most preferred. Calcium channel antagonists that do not freely cross the blood brain barrier are less preferred; these may be administered intrathecally to the brain and/or spinal cord, or intravitreally to the retina; most preferred among these antagonists are nifedipine, verapamil, nitrendipine, diltiazem, nicardipine, flunarizine, and diproteverine; oral or intraveous routes of administration may be effective.

The invention can reduce dementia, myelopathy, or vision loss associated with infection by a human immunodeficiency virus.

Other features and advantages of the invention will be apparent from the following description of the preferred embodiments thereof, and from the claims.

DESCRIPTION OF THE PREFERRED EMBODIMENTS

The drawings will first briefly be described.

Drawings

SELECTION OF CA++CHANNEL ANTAGONIST

Any suitable antagonist, generally, of neuronal voltage-dependent $Ca^{++}$channels may be used to reduce or prevent AIDS related vision loss, myelopathy, or dementia. Preferred calcium channel antagonists include, but are not limited to, the following drugs, of which the most preferred are those that are capable of crossing the blood brain barrier, for example, nimodipine (Miles Pharmaceuticals, West Haven, CT) Smith Kline drug no. 9512 (Smith Kline, French Beecham, Philadelphia, PA), and diproteverine (Smith, Kline, French-Beecham). Less preferred antagonists are those that are less CNS permeable, for example, verapamil (Calan, G.D. Searle & Co., Chicago, Ill.; Isoptin, Knoll, Whippany, NJ), nitrendipine, diltiazem (Cardizem, Marion, Kansas City, MO), and nifedipine, U.S. Pat. No. 3,485,847, hereby incorporated by reference (Procardia, L Pfizer, NY, NY; Adalat, Miles). Other $Ca^{2+}$channel antagonists which may be useful are mioflazine, flunarizine, bepridil, lidoflazine, CERM-196, R 58735, R-56865, Ranolazine, Nisoldipine, Nicardipine, PN200–110, Felodipine, Amlodipine, R-(−)-202-791, and R-(+) Bay K-8644 (Miles, Bayer), whose chemical formulae are described in Boddeke et al., Trends in Pharmacologic Sciences (1989) 10:397 and Triggle et al., Trends in pharmacologic Sciences (1989) 10:370.

For any given calcium channel antagonist, effectiveness in preventing neurological disorders associated with HIV-1 (or other HIV) infection is determined by screening the drug using one or more of the following assays of neuronal cell function; i.e., neuronal cell death, detection of intracellular free $Ca^{2+}$ion concentration in neurons, and detection of current flow through $Ca^{2+}$channels An effective antagonist will cause a decrease in HIV-1-associated neuronal cell death, and will prevent the rise in intracellular $Ca^{2+}$ion concentration that occurs in the presence of gp120. In addition, an effective antagonist will decrease $Ca^{++}$ion influx through neuronal calcium channels to a degree sufficient to reduce neuronal cell death, while not completely blocking $Ca^{++}$ion influx, an event which itself might kill neuronal cells. The antagonist may be compounded into a pharmaceutical preparation, using pharmaceutical compounds well-known in the art; the exact formulation of the anagonist compound depends upon the route of administration.

ASSAYS FOR NEURONAL CELL FUNCTION AND DEATH

An antagonist may be tested for utility in the method of the invention using any type of neuronal cell from the central nervous system, using the following assays, as long as the cell can be isolated intact using conventional techniques. Retinal cultures were used in the following assays (but hippocampal cortex neurons have also been used, e.g., in assays of neuronal death and intracellular calcium), because they can be produced from postnatal mammals, are well-characterized, and contain a central neuron, the retinal ganglion cell, that can be unequivocally identified with fluorescent labels. A substantial portion of retinal ganglion cells in culture display both functional synaptic activity and bear many, if not all, of the neurotransmitter receptors found in the intact retina.

GP120 INCREASES NEURONAL CELL DEATH IN VITRO

Neuronal cell death was assayed by incubating retinal ganglion cells in vitro with purified native or recombinant gp120 and scoring live cells. The ability of the $Ca^{2+}$ channel antagonist to reduce neuronal cell death was determined by scoring live cells which had been incubated with both gp120 and the antagonist.

Retinal ganglion cells from postnatal rats were identified and their viability ascertained as follows. Under general anesthesia, the fluorescent dye granular blue (Mackromolekulare Chemic, Umstadt, FRG) was injected as approximately a 2% (w/v) suspension in saline into the superior colliculus of 4- to 7-day-old Long Evans rats (Charles River Laboratory, Wilmington, MA). Two to 7 days later, the animals were killed by decapitation and enucleated, and the retinas quickly removed. The retinas were dissociated and cultured in Eaqle's minimum essential medium (MEM, catalog #1090, Gibco Grand Island, NY), supplemented with 0.7% (w/v) methylcellulose, 2 mM glutamine, 1 µg/ml gentamicin, 16mM dextrose, and 5%(v/v) rat serum, as described in Lipton et al., 1987, J. Physiol. 385:361. The cells were then plated onto 75 mm² glass coverslips coated with poly L-lysine in 35 mm tissue culture dishes; gp120 was then added. Sibling cultures received various doses of gp120, gp120 plus $Ca^{2+}$ channel antagonists, or no drugs at all.

Two native isolates of gp120, RF2 and 3B, obtained from (Brenneman et al., 1988, supra; Nature 335:445; National Cancer Institute, Fredrick, MD) were purified by immunoaffinity chromatography, as described by Robey et al. (1986, Proc. Nat. Aca. Sci. 83:7023), Pyle et al. (1988, AIDS Res. Hum. Retrovir. 3:387), and Kornfeld et al.(1988, supra). In addition, recombinant gp120 derived from the gene encoding gp120-3B, was obtained as follows.

Recombinant gp120 was produced by transfection of a Chinese Hamster Ovary (CHO) cell line (ATCC) with a plasmid containing isolate 3B envelope coding sequences encoding amino acids 61-531 (Lasky et al., 1986, Science 233:209). The gene was truncated to remove the native amino-terminal signal sequence and the carboxy terminal transmembrane domain, and then ligated in frame to the herpes simplex virus glyoprotein-D signal sequence (Berman et al., 1985, Science 227:1490) to allow the envelope protein to be constituitively secreted by the CHO cell line. Production in a mammalian cell ensured that the envelope protein was glycosylated. This envelope glycoprotein, rgp120-3B, was purified by immunoaffinity chromatography to 5 parts in a million (99.995%) pure based on estimates from polyacrylamide gel electrophoresis and Western blotting. The preparations of gp120 (at low concentrations) were highly labile in that they had to be freshly thawed (with refreezing avoided) in order to display activity.

Cell survival was assayed after one day in culture. Incubations lasted 20–24 h at 37° C. in an atmosphere of 5% $CO_2$/95% air. Ganglion cells could be unequivocally identified by the continued presence of the fluorescent blue dye. The ability of retinal ganglion cells to take up and cleave fluorescein diacetate to fluorescein was used as an index of their viability as described in detail in Hahn et al., 1988, supra. Dye uptake and cleavage correlates well with normal electrophysiological properties assayed with patch electrodes.

To perform the viability test, the cell-culture medium was exchanged for physiological saline containing 0.0005% fluorescein diacetate for 15–45 s, and then cells were rinsed in saline. Retinal ganglion cells that did not contain the fluorescein dye (and thus were not living) often remained visible under both phase contrast and UV fluorescence optics, the latter because of the continued presence of the marker dye granular blue; other dead retinal ganglion cells had disintegrated and only debris remained. In contrast, the viable retinal ganglion cells displayed not only a blue color in the UV light but also a yellow-green fluorescence with filters appropriate for fluorescein. Thus, the use of two exchangeable fluorescence filter sets permitted the rapid determination of viable ganglion cells in the cultures, which were found as solitary neurons or lying among other cells in small clusters (usually in the ratio of approximately 1:10 solitary to clustered).

Figure 1:
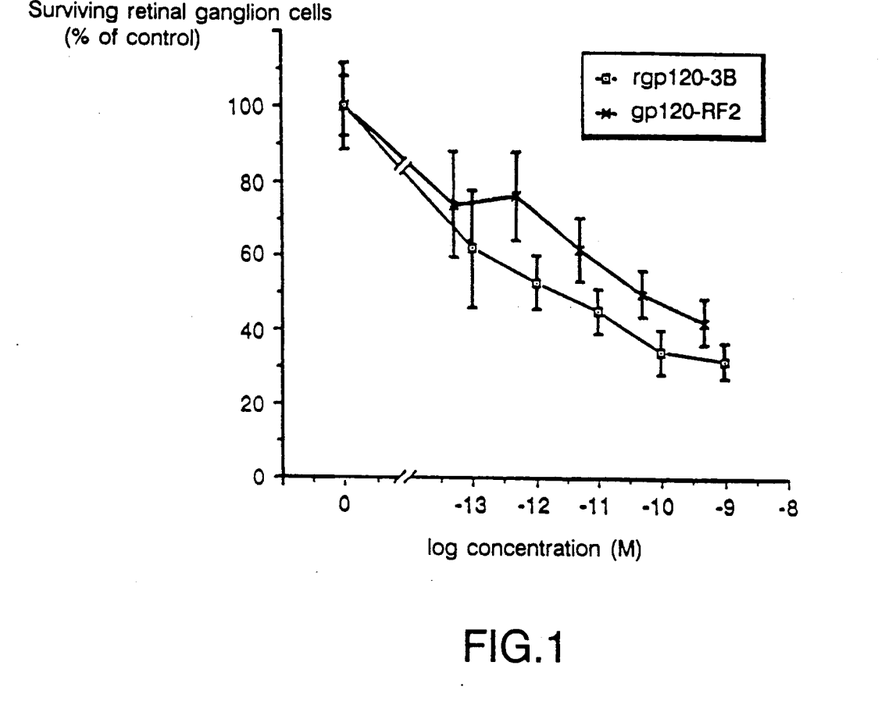
FIG. 1 is a dose response curve showing retinal ganglion cell death at different gp120 concentrations.

FIG. 1 is a dose response curve for concentrations of gp120 ranging from $10^{-9}$ M to less than $10^{-13}$ M, and shows that incubation of native purified gp120 (RF2) or recombinant gp120 preparations with cultured retinal cells resulted in the death of a significant number of ganglion cells within 24 h. A significant increase ($P<0.01$) in cell death was observed at gp120 concentrations above $2\times10^{-12}$ M Living cells were scored without knowledge of treatment in each culture. Control cultures had counts ranging from 95 to 250 retinal ganglion cells per 75 mm² coverslip, which corresponds to approximatley 1% of the total retinal cell population. Each point was determined in at least triplicate in each experiment, and the data represent 3 experiments. Values shown are means +/− their standard errors. Statistical analysis consisted of a one-way analysis of variance followed by a Scheffe multiple comparison of means. These results indicate that neuronal cell death in this experiment was due to the addition of gp120. To confirm this result, a control experiment was done in which neuronal cell death was prevented by the addition of antiserum specific for the gp120 envelope protein.

GP120 ANTISERUM PREVENTS GP120-ASSOCIATED NEURONAL CELL DEATH

Goat anti gp120 immune sera were prepared by primary and secondary intramuscular immunizations of recombinant fragments of the 3B isolate of gp120 plus Freund's adjuvant. Prior to these injections, preimmune serum was collected from each goat. The presence of gp120 antibodies in the postimmune serum was verified by polyacrylamide gel electrophoresis of immunopurified gp120 and Western blotting.

Figure 2:
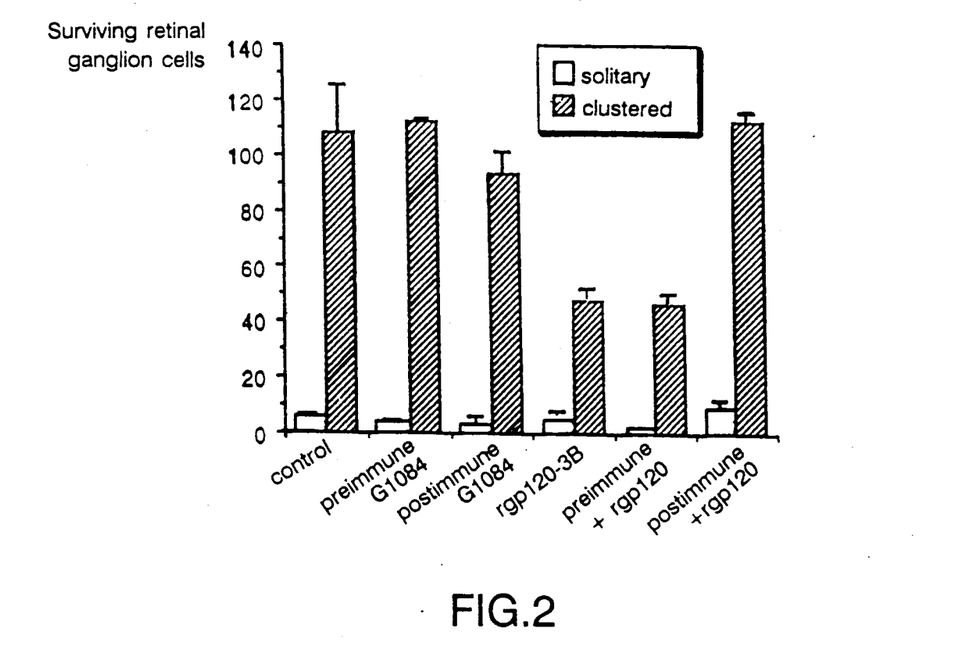
FIG. 2 is a graph of retinal cell survival in the presence of recombinant gp120 and antiserum.

FIG. 2 shows that anti gp120 sera prevent neuronal cell killing of rat retinal ganglion cells by recombinant envelope protein (rgp120-3B). Retinal cultures from 8 day-old rats were plated in the presence or absence of 20 pM gp120 plus either postimmune serum containing polyclonal gp120 antibodies from goat G1084, or preimmune serum from the same goat. Sera were used at a concentration of 1:500 diluted in control growth medium. FIG. 2 represents data from 5 separate assays. Error bars represent standard error of the mean. Statistical analysis was performed as described above. The results show that anti-gp120 neutralizes the effect of purified preparation of gp120; that is, cell death in cultures treated with 20 pM gp120 could be prevented by the addition of goat anti-gp120 serum to the culture medium. Neither the antibody preparation or its preimmune serum alone significantly affected survival compared to that observed in control culture medium. In contrast, the addition of gp120 or gp120 plus preimmune serum resulted in significant killing of retinal ganglion cells ($P<0.01$). Furthermore, compared to cultures treated with gp120 alone or gp120 plus preimmune serum, the two antibody preparations saved a significant proportion of retinal ganglion cells exposed to gp120 ($P<0.01$). Treatment with antiserum G1084 in the presence of gp120 resulted in neuronal cell counts that were not statistically different from cultures incubated in control medium alone. These figures present results for both solitary and clustered cells in culture; however, the most germane results are those for clustered cells, since neurons are interconnected in the brain.

GP120 AFFECTS THE INTRACELLULAR CONCENTRATION OF $CA^{2+}$

Gp120-promoted neurotoxicity was shown to involve an increase in intracellular $Ca^{2+}$ concentration in the following experiment.

The concentration of intracellular free $Ca^{2+}$ [$Ca^{2+}$] was measured in postnatal rat retinal ganglion cells and hippocampal neurons by digital imagine microscopy with the $Ca^{2+}$ sensitive fluorescent dye fura 2, as follows. Retinal ganglion cells were cultured from 1-to 2-week-old Long Evans rats as described (Leifer, et al., Science 224, 303 (1984); Lipton et al., J. Physiol. 385, 361 (1987). The ganglion cells were identified by the presence of retogradely transported red fluorescent dyes (DiI or rhodamine labeled microspheres) or by morphological and immunofluorescence criteria (e.g., the large or $\alpha$-like ganglion cells stain with neurofilament antibodies; Lipton et al., Nature 309, 624, 1984). During $Ca^{2+}$ measurements, unless otherwise stated the fluid bathing the neurons consisted of Hank's balanced salts; 136.7 mM NaCl, 1 mN NaHCO$_3$, 0.34 mM Na$_2$HPO$_4$, 0.44mM KH$_2$PO$_4$, 5.36 mM KCl, 2.5 mM CaCl$_2$, 0.5 mM MgSO$_4$, 0.5 mM MgCl$_2$, 5 mM Hepes NaOH, 22.2 mM glucose, and phenol red indicator (0.001% v/v); pH 7.2. Coat protein gp120 and other substances were usually applied to the neurons by pressure ejection after dilution in this bath solution. High K+solutions were prepared by substituting KCl for NaCl. Neuronal [$Ca^{2+}$] was analyzed with fura 2-acetoxy methyl ester (AM) as described [Grynkiewicz, et al., J. Biol. Chem. 260, 3440 (1985); Williams et al., Nature 318, 558 (1985); Connor et al., J. Neurosci. 7, 1384 (1987); Connor et al, Science 240, 649(1988); Cohan et al., J. Neurosci. 7, 3588 (1987); Mattson, et al., ibid, 9, 3728 (1989)]. After adding Eagle's minimum essential medium containing 10 $\mu$M fura 2-AM to retinal or hippocampal cell neurons, the cultures were incubated at 37° C. in a 5% CO$_2$/95% air humidified chamber and then rinsed. The dye was loaded, trapped, and deesterified within 1 hour, as determined by stable fluorescence ratios and the effect of the $Ca^{2+}$ ionophore ionomycin on measured [$Ca^{2+}$]. During $Ca^{2+}$ imagine, the cells were incubated in a solution of Hepes-buffered saline with Hank's balanced salts. The [$Ca^{2+}$]i was calculated from ratio images that were obtained by measuring the fluorescence at 500 nm that was excited by 350 and 380 nm with a DAGE MTI 66 SIT camera mounted on a Zeiss Axiovert 35 microscope. Exposure time for each picture was 500 ms. Analysis was performed with a Quantex (Sunnyvale, CA) QX7-210 image-processing system. Since cells were exposed to ultraviolet light only during data collection (generally less than a total of 20 s per cell), bleaching of fura 2 was minimal. Application of 200 pM of highly purified gp120 from a recombinant source, as described above, produced a striking increase in a [$Ca^{2+}$] (FIG. 3). Compared to control levels ($Ca^{2+}=63\pm4$ nM, mean $\pm$SEM, n=42) obtained before the addition of coat protein, levels increased 33 fold within 7 min of gp120 application (2100$\pm$330 nM, n=10; range of values 934 to 3943 nM). Other preparations of gp120 purified from natural isolates (RF2 and 3B) produced similar results. All experiments shown here used the highly purified recombinant gp120.

Similar effects were seen when gp120 was applied to hippocampal neurons. Hippocampal cortices of embryonic day 18 CD rats were dissociated with trypsin (0.027% w/v) and plated at a density of 600,000 cells per 35-mm culture dish, each dish containing five poly L lysine coated glass coverslips. Growth medium [Rosenberg et al., Neurosci., Lett., 103, 162 (1989)] was changed three times per week. In these experiments, $Ca^{2+}$ measurements were made after 14 to 21 days in culture. Overall, 200 pM gp120 produced an increase in [$Ca^{2+}$] in 76% of the neurons tested (n=75).

Several experiments indicated that gp120 was responsible for this rise in [$Ca^{2+}$]i Application of normal bathing medium did not produce a change in [$Ca^{2+}$]i, although subsequent addition of gp120 to the same retinal ganglion cell neurons increased [$Ca^{2+}$]i to $\sim 2\mu$M (n=10). Treatment of gp120 with trypsin followed by neutralization with soybean trypsin inhibitor (Sigma Chemical Co.) resulted in a preparation that was no longer active in increasing [$Ca^{2+}$]i. As the recombinant gp120 was produced from a construct with the herpes simplex virus glycoprotein D signal sequence, we applied glycoprotein D, made in exactly the same medium as recombinant gp120, to retinal ganglion cells (n=6). Glycoprotein D exerted either no effect or resulted in a modest increase in [$Ca^{2+}$] (<200 nM, n=6), but never to the micromolar level typically observed after the addition of equimolar gp120.

Figure 3A:
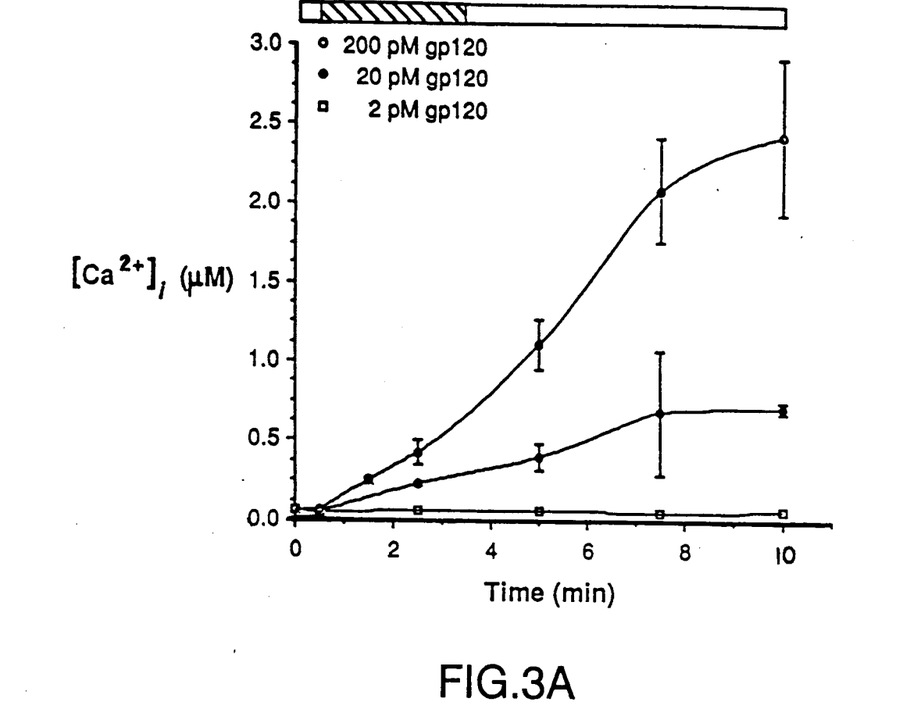
FIG. 3(a) is a graph of kinetics of intracellular free $Ca^{2+}$concentration ($[Ca^{2+}]i$) in a retinal ganglion cell in response to various doses of gp120, and (b) is a steady state dose response graph of gp120 concentration versus $[Ca^{2+}]$.

Pressure ejection of 50 nM KCl on these neurons yielded an increase in [$Ca^{2+}$] to the range of 600 nM (600$\pm$99 nM, n=5). Brief exposures to KCl for 30 s to 3 min produced these levels of $Ca^{2+}$, which peaked within 1.5 min of the beginning of the addition and recovered to levels of $\sim$250 nM over the next few minutes (240$\pm$21 nM, n=5). In contrast, at least a 1 min addition of 200 pM gp120 was necessary to produce any rise in [$Ca^{2+}$], and the effect was persistent and irreversible during the course of an experiment on a single cell (10 to 30 min of [$Ca^{2+}$] monitoring, with measurements every 30 s). The time course of the change in [$Ca^{2+}$]i evoked by a 3 min application of various doses of gp120 is shown in FIG. 3A. The peak level was reached ~7 min after the beginning of the addition. Thus, there were both qualitative and quantitative differences in the observed increase in [$Ca^{2+}$] in response to $K^+$ as opposed to gp120.

Figure 3B:
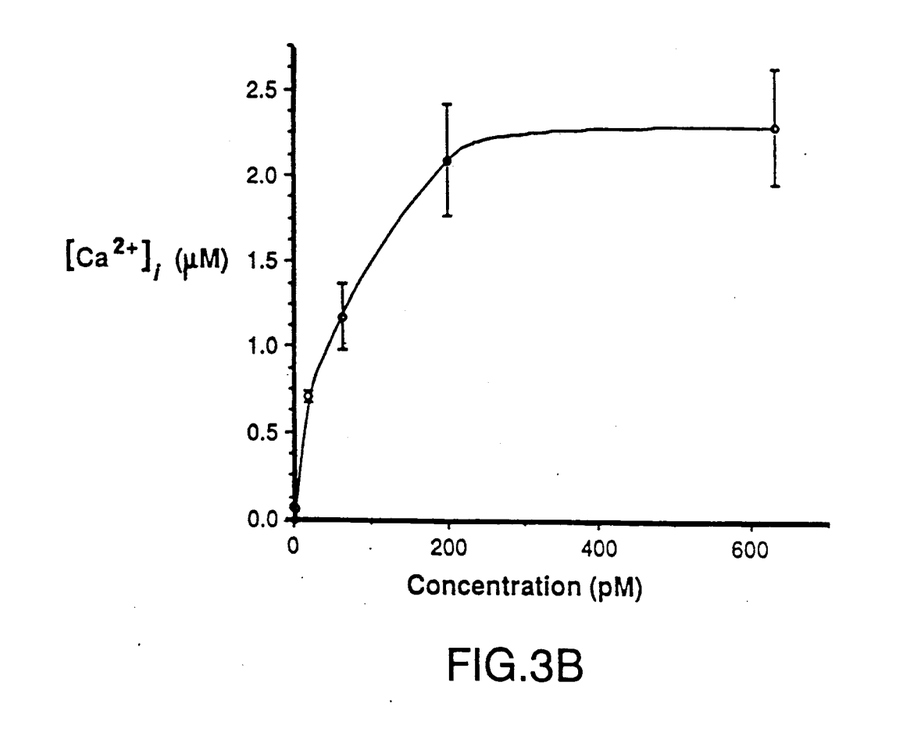

Extremely low doses of gp120, in the picomolar range, were effective in increasing [$Ca^{2+}$] in a graded, dose dependent fashion (FIG. 3B). As little as 20 pM gp120 produced increases in [$Ca^{2+}$]i. Very high levels of free $Ca^{2+}$ (>2 $\mu$M) were obtained with concentrations of gp120 at or above 200 pM.

The increases in [$Ca^{2+}$] observed with gp120 could still have been caused by a contaminant in the purified preparation of the viral envelope protein, although this seems unlikely with the highly purified recombinant gp120. As additional confirmation, we performed immunoprecipitation experiments with goat antibody to gp120 (anti gp120) coupled to protein A coated Sepharose beads.

Immunoprecipitation of gp120 was performed as described above with some modifications. A 1:100 or 1:500 dilution of anti gp120 or preimmune serum from the same goat, was bound to protein A coated Sepharose beads, washed, and incubated with a solution containing 7 nM gp120 for 18 hours at 4° C.; this was followed by centrifugation. The supernatant of the material treated with preimmune serum had gp120 activity as evidence by immunoblotting and by producing an increase in [$Ca^{2+}$] and cell death (after a dilution of 1:350 to ~20 pM); the material exposed to anti gp120 had little or no activity.

Figure 4:
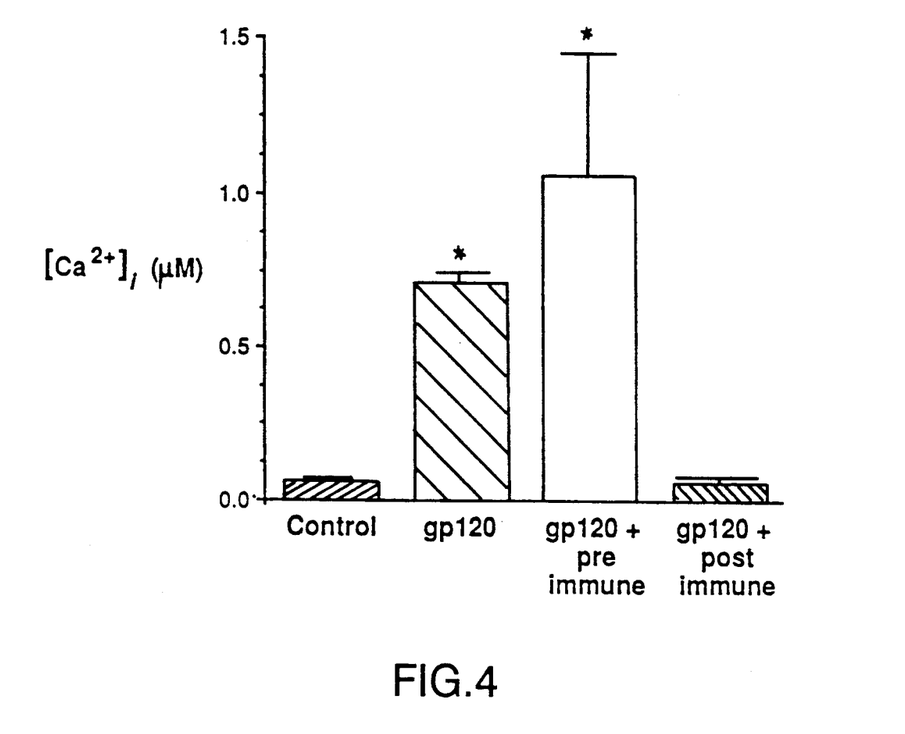
FIG. 4 is a bar graph of gp120 promoted rise in $[Ca^{2+}]$in the presence of gp120 alone or gp120 that has been immunoprecipitated with gp120 antiserum.

One of three such experiments is shown in FIG. 4. Treatment with preimmune serum did not significantly alter the ability of gp120 to increase [$Ca^{2+}$]i (compare striped and grey bars; although the mean [$Ca^{2+}$]i was greater after application of gp120 treated with preimmune serum than after gp120 alone, this difference did not reach statistical significance. Both gp120 and preimmune serum-treated gp120 produced a significant increase in [$Ca^{2+}$] compared to the control (P<0.01, analysis of variance (ANOVA) followed by Scheffe multiple comparison of means; significance indicated by an asterisk). In contrast, immunoprecipitation with postimmune serum containing anti-gp120 completely abrogated the gp120 effect (last column on right of FIG.).

GP120-PROMOTED NEURONAL CELL DEATH IS PREVENTED BY CALCIUM CHANNEL ANTAGONISTS

Nifedipine (500nM - 1$\mu$M) antagonizes the lethal effect of native gp120 isolates 3B and RF2 on retinal ganglion cells. In FIG. 5, cultures received gp120 (20pM) and/or nifedipine (10 $\mu$M) at the time of plating, and neuronal cell survival was assayed one day later. Each value is the mean obtained in 4 replicate tissue culture dishes. Survival of clustered retinal ganglion cells in the control group was significantly greater than those treated with gp120 (P<0.01). Compared to gp120 treated cultures, the addition of nifedipine significantly increased retinal ganglion cell survival (P<0.01). In comparison to the controls, exposure to 10 $\mu$M nifedipine alone resulted in cell death (P<0.05), although it was not to the same extent as that observed with gp120 alone. Moreover, in 20 of 22 trials, similar experiments revealed an increase in retinal ganglion cell survival with gp120 plus nifedipine treatment in comparison to gp120 alone, including 3B and RF2 natural isolates and the recombinant 3B form (significant at P<0.001, Sign test).

Figure 5A:
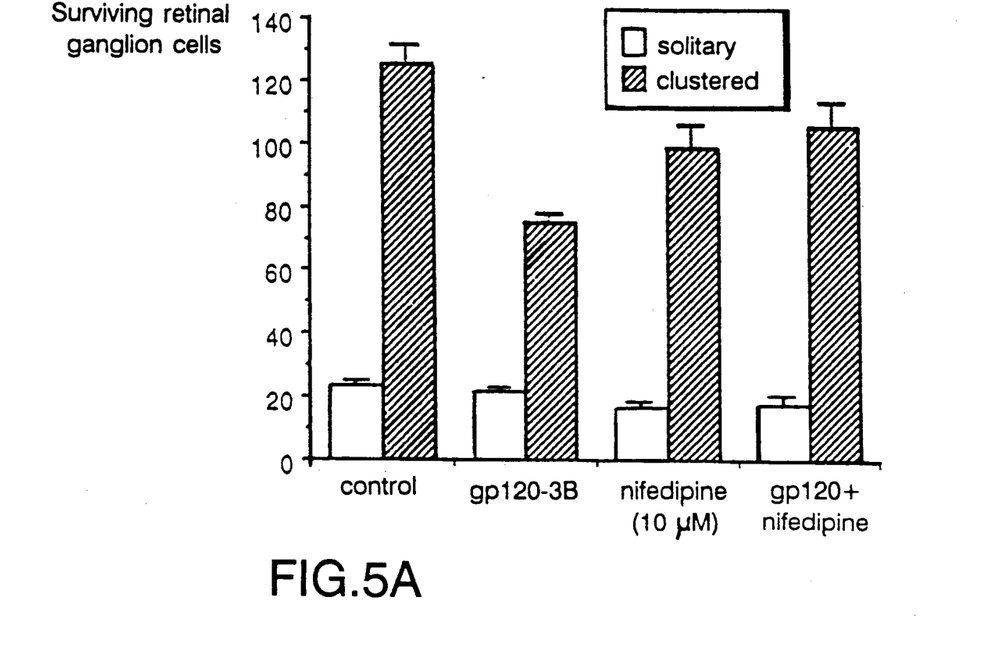
FIG. 5 is a graph of retinal cell survival in the presence of gp120 and/or 10μM nifedipine.
Figure 5B:
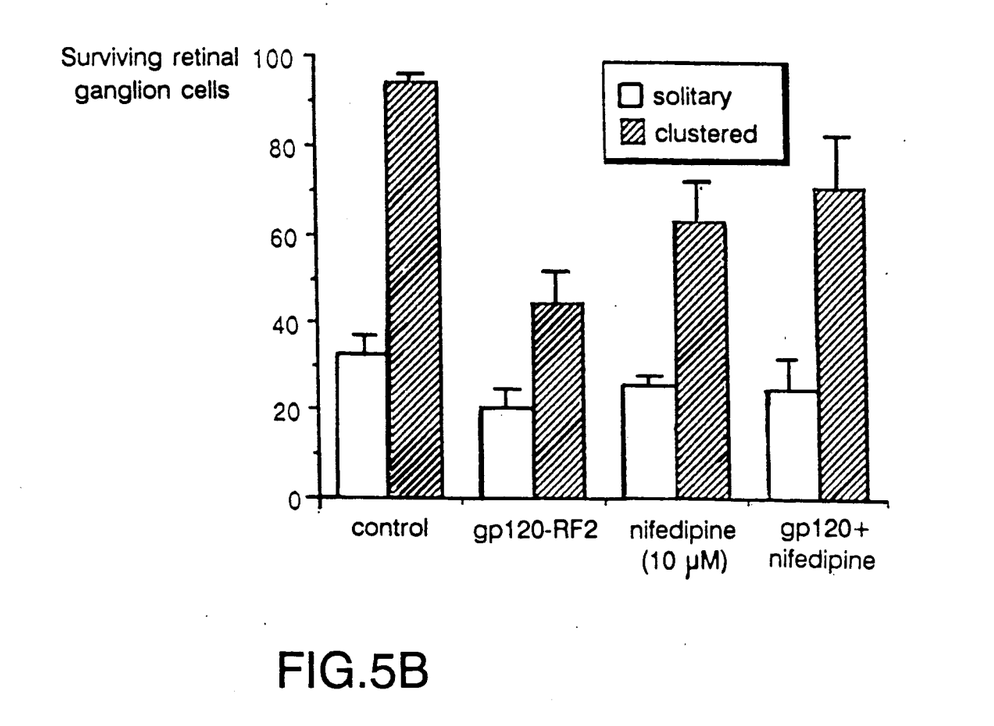

As shown in FIG. 5a, when 10 $\mu$M nifedipine was added with gp120-3B to the culture medium at the time of incubation, there was a significant decrease in neuronal killing compared to cultures treated with gp120-3B alone. Nifedipine attenuated neuronal death due to another purified isolate of gp120, RF2, in a similar fashion (FIG. 5b). Interestingly, this preventive effect occurred in spite of the fact that in 5 of 6 experiments (each with triplicate or quadruplicate samples), 10 $\mu$M nifedipine induced significant killing on its own compared to controls; in fact, in all six experiments, gp120 + nifedipine treated culture dishes had somewhat higher levels of survival than that observed with nifedipine alone (P<0.05, Sign test). One possible explanation for these phenomena invokes the hypothesis that there is an optimal level of intracellular $Ca^{2+}$ necessary for neuronal health and welfare. Too little $Ca^{2+}$ may inhibit survival (as seen here in the presence of nifedipine) while too much $Ca^{2+}$ may also lead to cell death (as evidenced by the effect of gp120 on $Ca^{2+}$ current) In between these two extremes (the "control" value of $Ca^{2+}$, or the $Ca^{2+}$ concentration in the presence of gp120 + nifedipine), survival may be enhanced. Alternatively, nifedipine alone could be toxic to these neurons for some other, unrelated reason, although in that case it would be difficult to explain the finding that survival was slightly better with the combination of gp120 plus 10 $\mu$M nifedipine compared to 10 $\mu$M nifedipine alone.

Figure 6A:
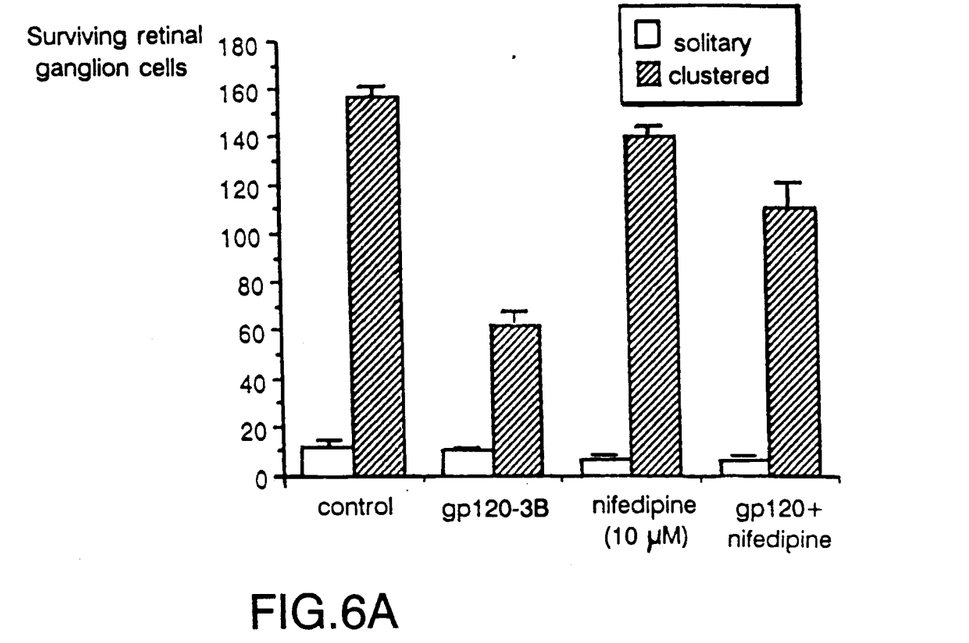
FIG. 6 is a graph of retinal cell survival in the presence of gp120 and/or 1μMM nifedipine or nimodipine.

The effect of using lower doses of calcium channel antagonists on neuronal survival following gp120 treatment is shown in FIG. 6. In FIG. 6a, a lower dosage (1$\mu$M) of nifedipine antagonizes the lethal effect of gp120 (20 pM) without substantial depression of retinal ganglion cell survival by the calcium channel antagonist itself. Treated cultures received gp120-3B (20 pM) and/or nifedipine (1 $\mu$M) at the time of plating, and retinal ganglion cell survival was assayed one day later. Incubation with gp120 resulted in neuronal cell killing compared to control sibling cultures (P<0.01). The presence of 1 $\mu$M nifedipine alone had substantially less detrimental influence on retinal ganglion cell survival than 10 $\mu$M (as observed in FIG. 5). Therefore, by fine tuning the dose response curve, it is possible to find an optimal level of calcium channel antagonist that produces minimal death on its own and yet substantially blocks the toxicity produced by gp120.

Figure 6B:
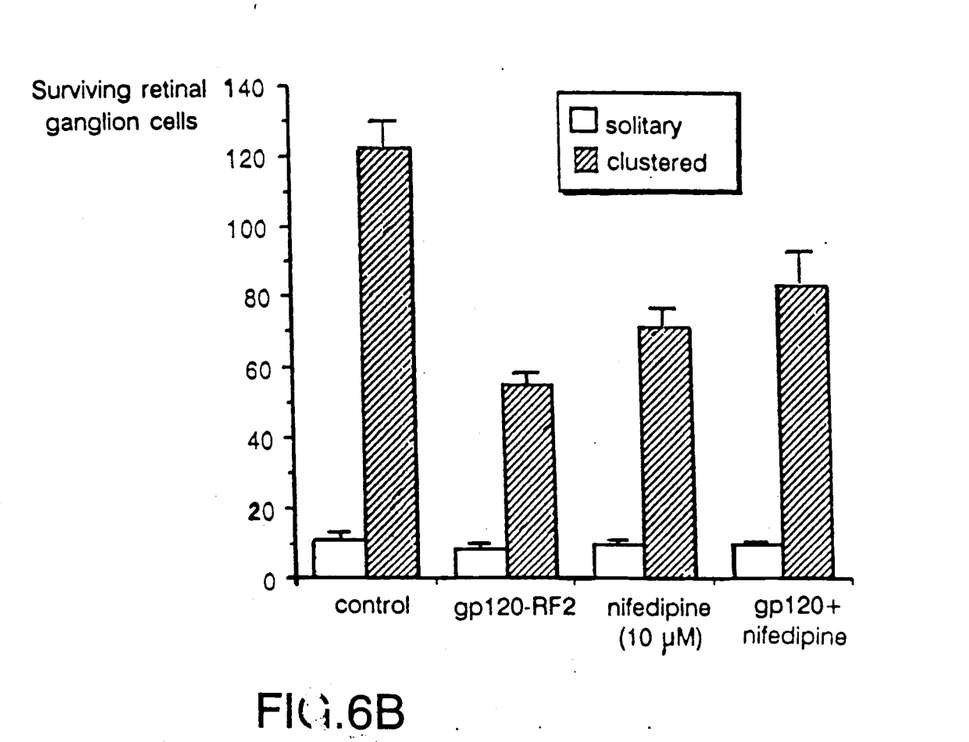

Therapeutic options for decreasing neuronal cell death due to HIV-I infection should include the use of other specific calcium channel antagonists, e.g., nimodipine, which has better CNS permeability than nifedipine (Allen et al., 1983, New Eng. J. Med. 308:619). FIG. 6b shows that treatment with 1 $\mu$M nimodipine significantly saved clustered retinal ganglion cells from gp120-induced death (P<0.01); however, 1 $\mu$M nimodipine produced killing by itself similar to that observed with 10 $\mu$M nifedipine (FIG. 5). FIG. 6a shows that lowering the concentration of nifedipine to 1 $\mu$M also resulted in a decrease in gp120-induced cell death; and, at this concentration, treatment with nifedipine alone did not result in neuronal cell killing. Taken together, the results with nifedipine and nimodipine demonstrate that the dosage of calcium channel blockers is obviously an important parameter; too high a concentration appears to harm normal neurons in the absence of gp120.

Figure 7:
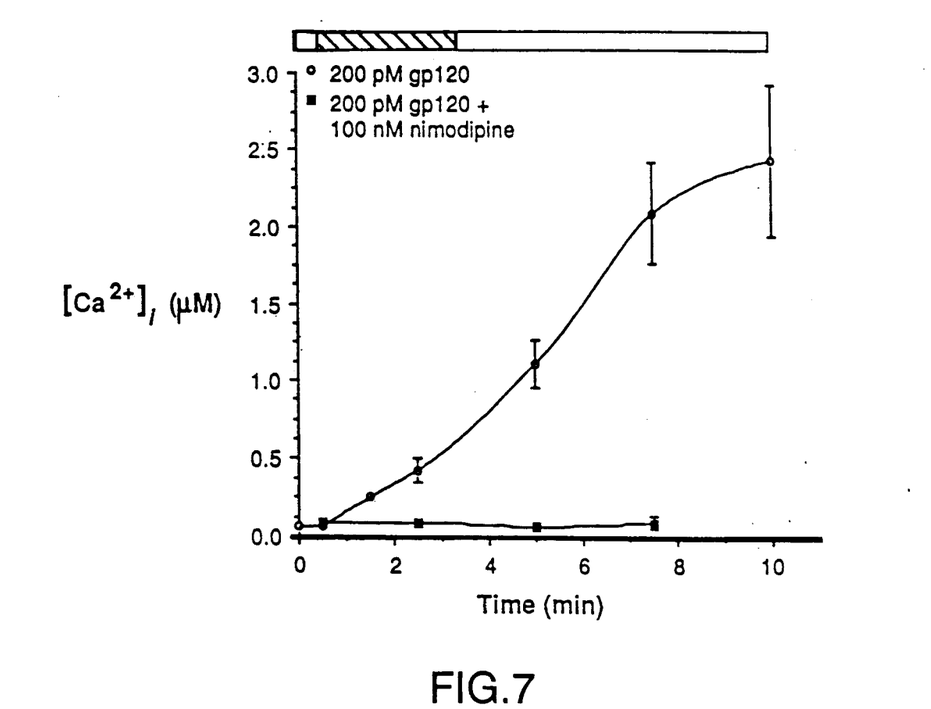
FIG. 7 is a graph of intracellular $[Ca^{2+}]$in the presence of gp120 and the $Ca^{2+}$channel antagonist nimodipine.

FIG. 7 shows the effect of 100 nM nimodipine on the intracellular concentration of free $Ca^{2+}$ ions in retinal ganglion cells incubated with gp120. The cells were loaded with fura 2, as described above. The viral envelope protein gp120 (200 pM) was applied by puffer pipette to neurons previously bathed in normal medium or in medium containing 100 nM to 1 $\mu$M nimodipine for several min. In FIG. 7, for neurons bathed in normal calcium medium (O; n=10), gp120 produced an increase in $[Ca^{2+}]$ as expected. In contrast, after treatment with nimodipine (lO; n=11), gp120 did not elicit a significant increase in $[Ca^{2+}]$.

CURRENT-FLOW IN THE PRESENCE OF GP120 IS INHIBITED BY CALCIUM CHANNEL ANTAGONISTS

The following assay of neuronal cell function tests the effect of calcium channel antagonists on $Ca^{2+}$ ion flow through $Ca^{2+}$ channels. Without being bound to any theory as to the mechanism whereby gp120 increases cell death, it is possible that gp120 increases current flow across $Ca^{2+}$ channels As a precautionary measure in screening for a compound capable of reducing the gp120 associated rise in intracellular $Ca^{2+}$ concentration, the following assay of $Ca^{2+}$ current should be performed in the presence of gp120.

Figure 8A:
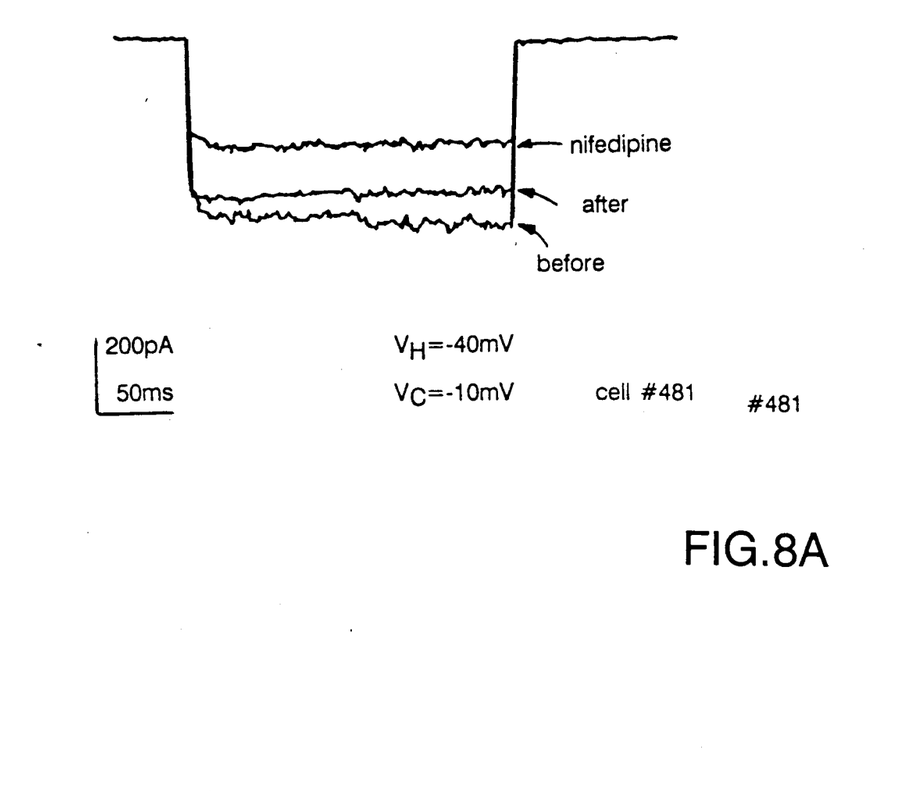
FIG. 8(a) shows current flowing through calcium channels in the presence of nifedipine and gp120, and (b) is a graph of the current-voltage relationship.
Figure 8B:
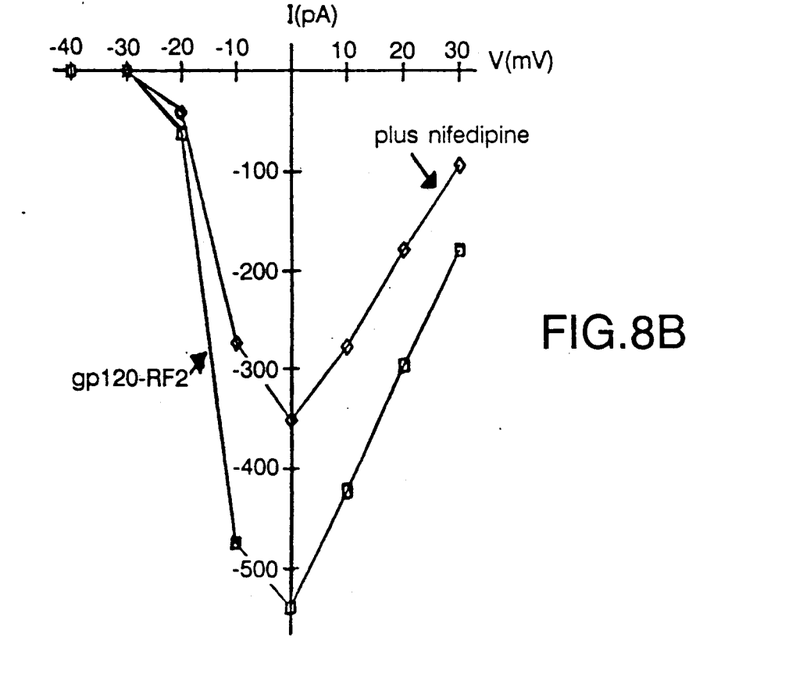

FIG. 8 shows that nifedipine suppresses $Ca^{2+}$ currents in the presence of gp120 in retinal ganglion cells. In FIG. 8a, in another neuron, nifedipine (10 $\mu$M) partially antagonized the current carried by $Ba^{2+}$ through calcium channels during the application of 20 pM gp120-RF2. All three traces were obtained in the presence of gp120. Inhibition by nifedipine was especially apparent (53% decrease) when the voltage step (in this case, $V_C = -10$ mV) was initiated from a depolarized holding potential ($V_H = 40$ mV); this observation is consistent with the action of calcium channel blockers on $Ca^{2+}$ current in other tissues. FIG. 8b shows the I-V relationship for the same cell as in FIG. 8a, and illustrates the effect of nifedipine at various test potentials in the continued presence of 20 pM gp120 RF2. Recording conditions use barium as the charge carrying species. A similar concentration range for antagonism of $Ca^{2+}$ current with nifedipine (100 nM-10$\mu$M) was obtained with nimodipine (100nM-10$\mu$M).

OTHER NEURONS ARE SENSITIVE TO GP120

Another important consideration is whether or not $Ca^{2+}$ levels in mammalian central neurons other than retinal ganglion cells will be sensitive to gp120 and, therefore, amenable to treatment with calcium channel blockers. Miller (1987, Science 235:46) suggests that dihydropyridines affect $Ca^{2+}$ influx, at least to some degree, in over 90% of neurons from various brain areas; there were, however, regional differences in the effectiveness of these drugs. Other classes of calcium channel antagonists, such as phenylalkylamines, may prove effective in different areas of the brain. For example, the $Ca^{2+}$ current in hippocampal neurons has been shown to be partially suppressed by verapamil (100 $\mu$M) (Yaari et al., 1987, Science 235:680); in addition, novel calcium channel blockers or G proteins and intracellular messengers that affect their efficacy, may prove useful in this regard (Olivera et al., 1985, Science 230:338, Dolphin et al., 1987 J. Physiol. 386:1; and Yaari et al., 1987, Science 238:1288). Miller (suora) showed that hippocampal neurons were more sensitive to calcium channel antagonists than were striatal neurons. This variability can probably be attributed to the fact that only a prolonged component of $Ca^{2+}$ current (similar to L-type current) is sensitive to dihydropyridines.

USE

Antagonists of the invention may be administered by any one of a number of routes; for example, for a CNS permeable antagonist such as nimodipine or Smith Kline drug no. 9512, nicardipine, flunarizine, or diproteverine, administration may be oral or intravenous, at a divided dosage of 60 to 1200 mg/day. For less CNS permeable antagonists, administration may be intrathecally or intravitreally, but oral or intravenous administration may be effective especially in the presence of break-down of the blood brain barrier in sick patients; nifedipine is adminstered at a dosage of 20 to 800 mg/day; verapamil is administered at a dosage of 80 to 720 mg/day; and diltiazem is administered at a dosage of 60 to 960 mg/day.

I claim:

1. A method of reducing death of CNS neurons in a human patient infected with a human immunodeficiency virus, comprising administering to said patient a compound capable of reducing the gp120 responsive rise in free $Ca^{++}$ ion concentration in said CNS neurons of said patient, in a concentration effective to cause such reduction.

2. The method of claim 1 wherein the blood of said human patient contains antibodies to HIV 1.

3. The method of claim 1 wherein said human patient manifests symptoms of the AIDS related complex or acquired immune deficiency syndrome.

4. The method of claim 1, said compound being capable of crossing the blood brain barrier.

5. The method of claim 1, said compound being nimodipine or Smith Kline drug no. 9512.

6. The method of claim 1, said nimodipine being administered to said patient orally or intravenously.

7. The method of claim 1, said compound being administered to said patient intrathecally or intravitreally.

8. The method of claim 1, said compound being one or more of nifedipine, verapamil, nitrendipine, or diltiazem.

9. The method of claim 5, in which said compound is nimodipine.

10. The method of claim 1, said compound being nicardipine, flunarizine, or diproteverine.

* * * * *